United States Patent [19]
Makower et al.

[11] Patent Number: 5,324,306
[45] Date of Patent: * Jun. 28, 1994

[54] HEMOSTATIC IMPLANT INTRODUCER

[75] Inventors: Joshua Makower, Nanuet, N.Y.; Claude A. Vidal, Santa Barbara, Calif.; Steven R. LeMott; Rodney E. Wells, both of East Lyme, Conn.; Thomas F. Banks, Santa Barbara, Calif.

[73] Assignee: Howmedica, Inc., New York, N.Y.

[*] Notice: The portion of the term of this patent subsequent to Mar. 1, 2011 has been disclaimed.

[21] Appl. No.: 68,199

[22] Filed: May 28, 1993

Related U.S. Application Data

[60] Division of Ser. No. 912,921, Jul. 13, 1992, which is a continuation-in-part of Ser. No. 784,920, Oct. 30, 1991, abandoned.

[51] Int. Cl.⁵ .............................................. A61B 17/12
[52] U.S. Cl. ..................................... 606/213; 604/57; 604/60; 604/63; 606/108
[58] Field of Search .................. 128/887, 8; 604/1, 11, 604/14, 15, 18, 21, 48, 52, 53, 57, 59, 63, 104, 117, 158, 160, 161, 171, 174, 264, 285, 278, 309, 368, 60, 61; 606/1, 108, 151, 154, 213

[56] References Cited

U.S. PATENT DOCUMENTS

| | | |
|---|---|---|
| 4,838,280 | 6/1989 | Haaga . |
| 4,852,568 | 8/1989 | Kensey . |
| 4,871,094 | 10/1989 | Gall et al. . |
| 4,890,612 | 1/1990 | Kensey . |
| 4,900,303 | 2/1990 | Lemelson . |
| 4,929,246 | 5/1990 | Sinofsky . |
| 4,934,999 | 6/1990 | Bader . |
| 4,936,835 | 6/1990 | Haaga . |
| 4,973,301 | 11/1990 | Nissenkorn . |
| 4,995,868 | 2/1991 | Brazier . |
| 5,002,556 | 3/1991 | Ishida et al. . |
| 5,021,059 | 6/1991 | Kensey et al. . |
| 5,053,046 | 10/1991 | Janese . |
| 5,061,274 | 10/1991 | Kensey . |
| 5,108,421 | 4/1992 | Fowler . |
| 5,129,882 | 7/1992 | Weldon et al. . |
| 5,221,259 | 6/1993 | Weldon et al. . |
| 5,222,974 | 6/1993 | Kensey et al. . |

FOREIGN PATENT DOCUMENTS

482350  4/1992  European Pat. Off. .

*Primary Examiner*—Stephen C. Pellegrino
*Assistant Examiner*—Glenn Dawson
*Attorney, Agent, or Firm*—Haugen and Nikolai

[57] ABSTRACT

A puncture seal device for stemming the flow of blood from a punctured blood vessel includes an elongated outer sheath affixed to a generally tubular housing where the housing contains a manually actuable slide which is affixed to a rigid tubular pusher member coaxially disposed within the outer sheath. Also contained within the outer sheath in longitudinal alignment with the pusher and distally thereof is a ring-shaped plug of a hemostatic material. The assembly thus far described may be fitted over a tubular introducer or the body of a catheter and then advanced therealong until the distal end of the outer sheath is proximate a bleeding blood vessel. By actuating the pusher member, the hemostatic plug surrounding the introducer or catheter is ejected from the distal end of the outer sheath and held in abutting relationship to the bleeding blood vessel.

11 Claims, 5 Drawing Sheets

HEMOSTATIC IMPLANT INTRODUCER

CROSS-REFERENCE TO RELATED APPLICATION

This is a Divisional of copending application Ser. No. 07/912,921, filed on Jul. 13, 1992 which is a continuation-in-part application of Ser. No. 07/784,920, filed Oct. 30, 1991, and entitled "Hemostatic Implant Introducer", abandoned.

BACKGROUND OF THE INVENTION

I. Field of the Invention

This invention relates generally to a surgical instrument for use in intravascular catheterization procedures, and more particularly to devices for positioning a hemostatic agent against a puncture entry wound in a blood vessel to stem the flow of blood therefrom following removal of the catheter and catheter introducer at the conclusion of the procedure.

II Discussion of the Prior Art

When performing angiography or angioplasty procedures, following the Seldinger technique, the angiography catheter or angioplasty catheter is generally introduced into the vascular system by first employing a sharpened hollow needle to penetrate the skin, the underlying muscle tissue, and to enter the selected blood vessel. Next, a guidewire is commonly inserted through the lumen of the hollow needle and made to enter the selected blood vessel. Following that, the needle is stripped off the guidewire and a combination of a dilator and an introducer (or an introducer alone) are fed over the guidewire and pushed through the skin until first the dilator and next the introducer enter the selected blood vessel. The guidewire may next be removed, and the selected catheter for carrying out the procedure is fed through the lumen of the introducer and advanced through the vascular system until the working end of the catheter is appropriately positioned. Depending upon the procedure, a dye may be injected through the catheter or a balloon expanded. Following the conclusion of the catheterization procedure, the working catheter will be withdrawn and, subsequently, the combination dilator and introducer will also be stripped out of the wound.

Because it is common practice to administer a blood thinning agent to the patient prior to many of the procedures, a problem exists in stemming the flow of blood through the puncture wound made in the vein or artery. Typically, it is necessary to maintain pressure over the region for at least 30 minutes. Even more time is required if the patient is hypertensive or anticoagulated. When human hand pressure is utilized, it is somewhat wasteful of professional time. Devices, such as pressure bandages, sand bags or clamps may be employed, but for these devices to work, the patient must be compliant and motionless for this prolonged period. Also, with obese patients, because of the significant amount of tissue between the skin and the penetrated vessel, good hemostatic pressure oftentimes cannot be obtained above the penetrated artery or vein. Thus, a need exists for a means for accelerating hemostasis.

In U.S. Pat. Nos. 4,852,568 and 4,890,612 to Kenneth Kensey, a device and method is described for sealing puncture or incision wounds created percutaneously during a surgical procedure. In accordance with the teachings of the Kensey patents, a collagen plug having an anchoring mechanism in the form of a filament or string attached, is passed through the introducer following removal of the working catheter and is allowed to enter the blood vessel to be sealed. The introducer is then removed from the body and the string is tensioned until the collagen plug affixed to its end abuts the surgically-created opening in the blood vessel proximate its interior wall. When the collagen material is exposed to body fluids, it swells to create a block for the wound in the vessel wall while the collagen itself acts as a blood clotting agent and accelerates hemostasis.

Problems exist with the approach set out in the afore-referenced Kensey patents. More particularly, any intraluminal deposition of a collagen can result in embolization, especially as the material begins to reabsorb. Particles may break off and float downstream to the point where they may lodge in a smaller vessel, causing an infarct to occur. Not only that, but collagen material acts as a nidus for platelet aggregation which assists in blood clotting. Hence, the intraluminal deposition of a hemostatic agent can initiate a thrombosis at the site.

U.S. Pat. No. 4,838,280 and U.S. Pat. No. 4,936,835 to John R. Haaga teach the idea of incorporating a hemostatic material as a part of a needle biopsy device so that following the gathering of the tissue sample, a hemostatic plug can be left in the void in the tissue from which the sample had been excised. The collagen plug that is left behind serves as a hemostatic agent for more rapidly stemming blood flow from the point of injection of the biopsy needle.

Applicants are also aware of a product produced by Datascope Inc. of Montvale, N.J., and sold under the trademark "VASOSEAL". That device comprises a kit including a guidewire, a needle clip, a skin dilator, an outer syringe barrel, an inner plunger, and two cylinders of compressed collagen material. In carrying out the blood vessel sealing procedure using the VASOSEAL apparatus, two operators are required. Before the original puncture needle is removed, a clip is placed on the shaft of the needle at the skin level to mark the distance down to the artery. The needle and clip are then placed up against a card having graduations printed thereon and one of a plurality of device lengths are selected. When the catheterization procedure is completed, all devices are removed except for a guidewire. One operator is needed to maintain compression upstream while another operator works on the puncture site. A skin dilator is advanced over the guidewire into the tissue to the measured level. A syringe barrel is then advanced over the skin dilator to the same measured level. The dilator and the guidewire are then removed. Next, a plunger is loaded with one of the two plugs of collagen and this is inserted into the syringe barrel and advanced down into the wound. The plunger is removed and reloaded with a second collagen plug and this, too, is inserted down into the syringe barrel into the wound. The main operator now takes over the job of applying a compression force over the area and holds the spot for several minutes. When no bleed-back or hematoma growth is seen, the operator removes the syringe and plunger.

OBJECTS

It is accordingly a principal object of the present invention to provide an improved method and apparatus for effecting hemostasis in the course of a surgical procedure.

Another object of the invention is to provide an improved method and apparatus for plugging a surgically-created puncture in a blood vessel.

Yet another object of the invention is to provide an improved apparatus for deploying a hemostatic material against the exterior surface of a blood vessel at the point of a puncture opening therein.

Yet another object of the invention is to provide an apparatus for selectively displacing a coaxially mounted mass of a hemostatic material from a position in surrounding relationship relative to a tubular instrument that has been inserted through the puncture so that the mass assumes a position in abutting relationship relative to a puncture site on the exterior wall of a blood vessel.

Still another object of the invention is to provide a method and apparatus for effecting hemostasis of a puncture wound in a blood vessel in which a mass of a hemostatic material coaxially surrounding a tubular member is made to abut a puncture site in a blood vessel, but without any of the hemostatic material entering the luemen of the blood vessel nor without the need for an anchoring mechanism.

A still further object of the invention is to provide a surgical instrument for use during a catheterization procedure, a laparoscopic procedure or any other endoscopic procedure for installing a plug of a hemostatic material in abutting relation to the exterior wall of a blood vessel at a site where that blood vessel has been penetrated, the device being unobtrusive and easy to utilize by a single operator.

SUMMARY OF THE INVENTION

The foregoing features, objects and advantages of the invention are achieved by providing a first tubular member, which is adapted to be inserted into a surgically-creasted opening in a blood vessel, with a mass of a hemostatic material configured to coaxially surround the exterior of that tubular member. The term "tubular member", as used in this context, is intended to broadly describe any one of a dilator, an introducer, or a catheter. Coaxially surrounding the first tubular member with a predetermined clearance and shielding the plug from exposure to body fluids, principally blood, is an outer tubular sheath having a proximal end, a distal end, and a lumen extending therebetween. A means for ejecting the hemostatic mass in the form of a tubular pusher also surrounds the first tubular member and is contained within the lumen of the outer tubular sheath. A housing is affixed to the proximal end of the outer sheath and a slide, coupled to the pusher, is contained in the housing. In one embodiment, a protruding thumb pad is provided for applying a moving force to the slide. In another, a rack and pinion mechanism is employed to move the pusher relative to the hemostatic mass. By advancing the pusher in the distal direction, its distal end engages the coaxial disposed hemostatic mass and is used to force it outward of the lumen of the tubular sheath member so that it will abut the penetration site in the wall of the blood vessel.

In a modified arrangement, the hemostatic mass is annular in shape and is housed within an outer tubular sheath proximate the distal end of the sheath. The pusher is also tubular and has its distal end abutting the proximal end surface of the hemostatic mass within the outer sheath. The proximal end of the pusher extends beyond the proximal end of the outer sheath. In use, the instrument is threaded over the tubular member and its distal end is made to abut the exterior wall of the punctured blood vessel. To deploy the hemostatic mass, the pusher is held stationary while the outer sheath is pulled rearward, uncovering the mass. Then, the entire instrument can be stripped back off of the tubular member. To avoid accidental, premature ejection of the hemostatic mass, a suitable locking arrangement is used to couple the pusher to the outer sheath to prevent relative movement between these two parts until the lock is released.

In accordance with a further modified embodiment, the coaxially disposed mass, as well as the tubular sheath, the tubular pusher ad the housing supporting the sheath and pusher are longitudinally slit to allow the unit to be assembled onto the exterior of a tubular body from the side rather than using a coaxial approach.

The hemostatic mass may comprise a freeze-dried collagen, a cellulose gel material, such as a GEL-FOAM ®, a resorbable lactide/glycoside or other resorbable substance which by virtue of its chemical properties or its lattice construction functions as a hemostatic agent. It is preformed so as to fit within the confines of the tubular sheath member in surrounding or coaxial relationship to the first tubular member, but when deployed out through the distal end of the outer sheath member, will expand when contacting body fluids to form a predetermined shape configuration. The annular collagen plug is preferably a composite which is preformed to exhibit a distal, vessel puncture-contacting end that is highly hemostatic and a proximal region that is highly self-expanding. When released from the confines of the puncture sealing device (PSD), it swells to block the wound and to maintain itself in position.

DESCRIPTION OF THE DRAWINGS

A better understanding of the invention will be had by a reading of the following detailed description of the preferred embodiment, especially when considered in conjunction with the accompanying drawings in which like numerals in the several views refer to corresponding parts.

DESCRIPTION OF THE PREFERRED EMBODIMENT

In describing the construction and mode of operation of the present invention, it will be considered as being used in connection with the conduct of the Seldinger procedure for introducing a catheter into the lumen of a blood vessel. It is to be understood, however, that the invention may also be utilized in other surgical procedures, such as laparoscopic or other endoscopic procedures, wherein a tubular working instrument is routed through the lumen of a tube and where penetration of a blood vessel, such as a vein or artery, is likely to be encountered. Having described the present invention in connection with the Seldinger procedure, those skilled in the art will readily appreciate how the device and method may be employed in other related procedures.

Figure 1:
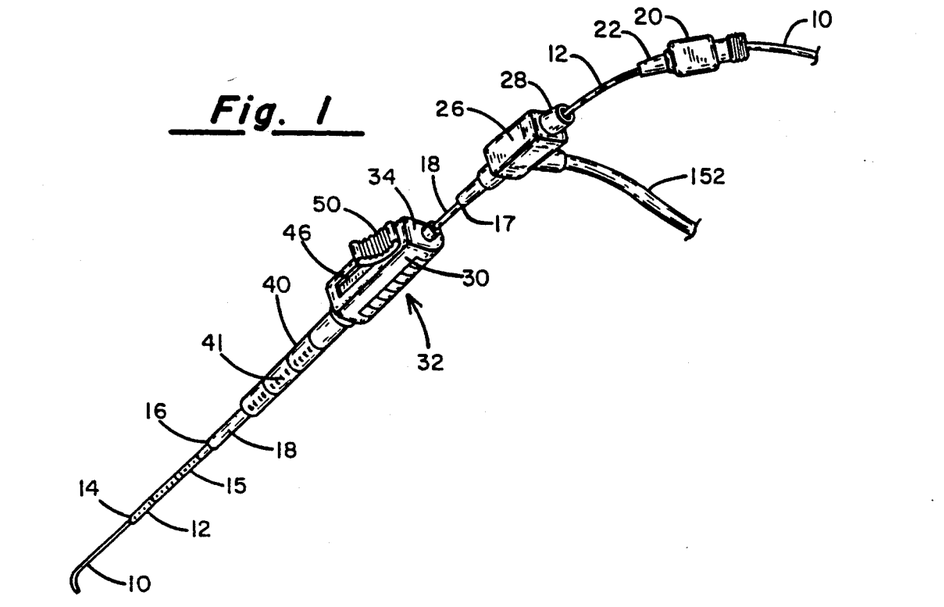
FIG. 1 is a longitudinal cross-sectional view illustrating the construction of a first preferred embodiment of a puncture sealing device.

Referring now to Figure there is shown a perspective view of the puncture sealing device (PSD) in accordance with a first embodiment of the present invention deployed on the conventional apparatus used in introducing a working catheter into the lumen of a blood vessel, such as the femoral artery. More particularly, as those skilled in the art appreciate, a hollow needle (not shown) having a sharpened distal end and graduated markings along its length is first pushed through the dermal layer and is made to enter the lumen of the femoral artery through a puncture wound created by the needle in the wall of that artery. The depth of the artery can be assessed by noting the markings on the needle at the point where blood is first exiting the needle. Next, a guidewire, identified by numeral 10, is inserted through the hollow needle into the artery and advanced a predetermined distance therein. The hollow needle is then stripped off the proximal end of the guidewire 10, and a dilator 12 may then slipped therealong in the distal direction until its tapered distal end 14 is made to enter the wound, enlarging it to the point where the distal end 16 of a tubular introducer 18 may also be made to enter the lumen of the selected blood vessel without creating a tear.

The stepped junctions between the guidewire and the distal end of the dilator and between the dilator and the distal end of the introducer, upon entering the opening in the blood vessel creates a noticeable tactile response to the operator. For reasons which will become more apparent when the method of operation is discussed, instead of having graduated markings on the puncture needle, the dilator 12 may have graduated measurements or markings on the exterior thereof as identified by numeral 15 in FIG. 1. When the distal end 14 of the dilator 12 enters the blood vessel, the tactile indication provided to the surgeon alerts him or her to glance at the portion of the dilator exposed above the skin to obtain a coarse estimate as to the distance beneath the skin at which the opening in the blood vessel is located.

Figures 2, 3A, 3B, 3C, 4, 5:
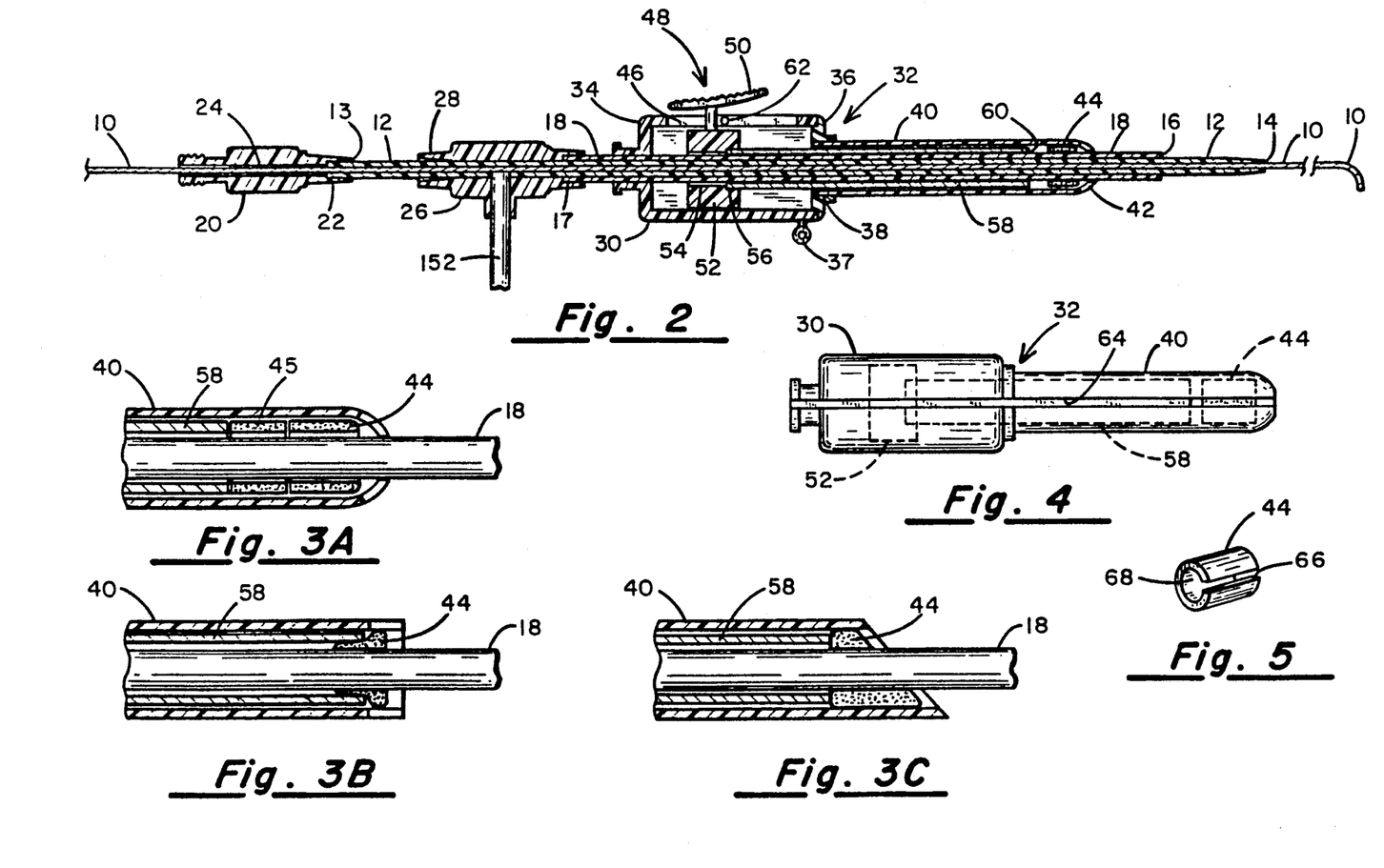
FIG. 2 is an enlarged, partial view of the distal end portion of the puncture sealing device of FIG. 1.
FIGS. 3A, 3B and 3C are enlarged, partial cross-sectional views of the distal end portion of the puncture sealing device having modified sheath configurations.
FIG. 4 is a bottom view of the puncture sealing device of FIG. 1, but modified in accordance with a second embodiment.
FIG. 5 is a perspective view of a hemostatic mass to be used with the embodiment of FIG. 4.

Referring still to FIG. 1 and the longitudinal cross-sectional view of FIG. 2, the proximal end 13 of the dilator 12 has a molded plastic hub 20 affixed thereto, the hub having a tapered distal nose portion 22 thereon. A longitudinal bore 24 extends through the hub to allow the guidewire 10 to pass. Likewise, the proximal end 17 of the tubular introducer 18 is secured within a socket formed in a molded plastic hub member 26. The hub has a tapered bore 28 in its proximal end for receiving the tapered nose 22 of the dilator, thus allowing the two parts to be releasably locked or joined relative to one another. Those skilled in the art will also appreciate that other known locking mechanisms can be incorporated on the PSD for releasably clamping that device to the tubular support (introducer or catheter) which the PSD surrounds. For example, the commonly used Touhy Borst clamp may be configured on the proximal end 34 of the PSD whereby simple rotation of a knob will lock or unlock the PSD to the tubular body 12 depending on the direction of rotation.

As can be seen from FIGS. 1 and 2, the guidewire 10, dilator 12 and introducer 18 are coaxially disposed relative to one another and extend through a housing member 30 which forms a part of the PSD indicated generally by numeral 32. The housing 30 has a proximal end 34 having an opening formed therethrough for receiving the tubular introducer 18. Also forming a part of the housing is a distal end cap 36. The tubular sheath or barrel member 40, like the dilator 12, is provided with graduated markings, as at 41, which permit the surgeon to insert the distal end of the sheath to a premeasured depth below the skin. As shown in FIG. 2, the proximal end 38 of a tubular sheath member 40 is fitted into the end cap 36 and is adhesively bonded or otherwise fixedly attached to the end cap 36. The inside diameter of the plastic sheath 40 is sized to provide a predetermined clearance between it and the outer surface of the introducer 18.

Contained within this clearance space and proximate the distal end 42 of the sheath 40 are one or more pieces 44 of a suitable hemostatic material which are preformed to assume a coaxial disposition relative to the introducer 18 or other "tubular member" as that term was earlier defined at page 5, supra. The material may be freeze-dried collagen, a cellulose gel, a resorbable polyglycolic acid composition or any suitable resorbable substance which, by virtue of its chemical composition or of its lattice construction, acts as a hemostatic agent. The mass 44 partially or fully surrounds and fits snugly against the outer diameter of the tubular introducer 18, within the confines of the sheath 40 where it remains generally isolated from contact with blood and other body fluids until deployed. By virtue of being in a compressed state until deployed, it is prevented from prematurely reacting with blood.

A longitudinal slot 46 is formed through the housing 30 allowing a thumb-operated slide assembly 48 to pass therethrough. The slide assembly includes a thumb pad 50 which is attached to a slide member 52 contained within the housing 30. The slide 52 includes a bore 54 through which the tubular introducer 18 may pass. The proximal end 56 of a generally rigid tubular pusher 58 is affixed to the slide 52 and, thus, is movable therewith. The distal end 60 of the tubular pusher is adapted to engage the proximal edge surface of the coaxially disposed hemostatic mass 44 when the slide is moved in the distal direction (to the right in FIG. 2).

A locking pin is shown as passing transversely through an aperture 62 across the slot 46 prevents inadvertent movement of the thumb slide assembly 48 and premature ejection of the hemostatic plug. Alternative locking arrangements are also envisioned, including placing a downwardly extending barb or latch on the proximal end of thumb pad 50 which cooperates with the proximal end 34 of housing 30 to prevent movement of the slide until the barb or latch is intentionally released. Those skilled in the art will recognize that other "safety" devices can be used to prevent unintended deployment of the hemostatic material from the barrel or sheath 40.

As is illustrated in FIGS. 2 and 3A, the distal end portion 42 of the outer tubular sheath 40 may be rounded or bullet-shaped and appropriately slit to more readily permit the coaxial plug(s) 44 to be ejected out from the nose 42 of the sheath 40 upon actuation of the slide assembly 48 to which the tubular pusher 58 is affixed. FIGS. 3B and 3C illustrate that the distal end of the tubular sheath 40 may be blunt or beveled and also that the hemostatic material, as at 44, may be preshaped into a desired configuration, with FIG. 3B showing a somewhat mushroom-shaped arrangement and FIG. 3C showing a beveled shape. A beveled tip on the distal end of the outer tubular sheath assists in cutting its way through the skin and subdural tissue in approaching the punctured blood vessel.

It is also possible to preform the hemostatic mass in other forms, including, for example, as a helix or a woven or braided structure, the prime requirement being that it can be coaxially disposed about a tubular member as previously explained. Upon exposure to body fluids upon release thereof from the sheath, the mass will swell to define a predetermined shape, e.g., rounded, blunt, frustoconical, beveled or mushroom.

In the arrangement shown in FIGS. 1 and 2, the device for placing the plug of hemostatic material against the exterior wall of a blood vessel at a point of puncture entry must be assembled onto the introducer and dilator before the assembly is threaded onto the guidewire. In the arrangement shown in FIG. 4, the plug placement instrument 32 is designed so that it can be placed onto the body of a tubular member at a time just prior to when the surgeon wishes to inject the hemostatic plug. More particularly, FIG. 4 is a bottom view of the instrument, i.e., the side thereof which is opposite to the thumb rest member 50. It can be seen that in the embodiment of FIG. 4, a longitudinal slit 64 is formed through the walls of the tubular sheath 40, the tubular pusher 58, the housing 30 and the slide 52. Furthermore, as shown in FIG. 5, the hemostatic mass 44 used with the embodiment of FIG. 4 is generally C-shaped having a slot 66 formed through its wall and communicating with the central opening 68 thereof. By providing the slots 64 and 66 in the respective pieces mentioned, the device of FIG. 4, loaded with one or more pieces of preshaped hemostatic material 44, may be assembled onto a tubular member such as an introducer, a working catheter used with an endoscope or other similar device by merely slipping it onto the tubular member from the side with the tubular member fitting into the respective slots 64 and 66. This may prove more advantageous than an over-the-wire installation of the loaded PSD.

ALTERNATIVE EMBODIMENT

Figure 6:
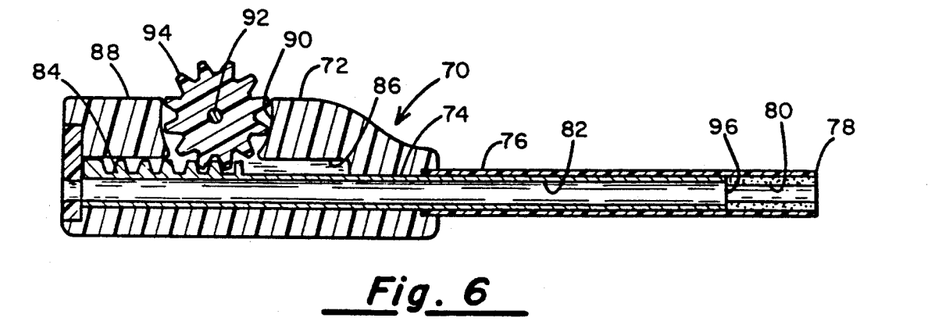
FIG. 6 is a side sectional view of the puncture sealing device in accordance with a third embodiment.

Referring now to FIG. 6, there is shown a further alternative embodiment of a PSD in accordance with the teachings of the present invention. In this view, the device is shown in longitudinal cross-section but does not include the coaxial arrangement of a guidewire, dilator and introducer as in the arrangement shown in FIGS. 1 and 2. It is to be understood, however, that the device of FIG. 6 is intended to be assembled on to a tubular member, either using an endwise over-the-wire approach or a side approach as with the earlier described embodiment. The PSD is indicated generally by numeral 70 and is seen to include a molded handle member 72, preferably formed from a medical-grade plastic. The handle 72 includes a longitudinal bore 74 in which is fitted the proximal end of a tubular outer sheath or barrel member 76. Contained within the lumen of the sheath 76 near its distal end 78 is a mass of hemostatic material 80 which is preshaped so that it can assume a coaxial relationship relative to a cylindrical tube or wire with which the PSD is to be used. Also disposed within the sheath or barrel 76 is a tubular pusher 82 which extends into and is slidingly received within the bore 74 in the handle 72. Integrally molded with or otherwise formed on the exterior surface of the tubular pusher 82 near its proximal end is a gear rack 84 which is dimensioned to fit within a key-way 86 extending radially outward from the bore 74. Extending inwardly from the surface 88 of the molded handle 72 is a recess 90 having a generally circular profile. Fitting into the recess 90 and journaled for rotation about a pin or axis 92 is a pinion gear 94 whose teeth engage the rack 84.

It is apparent from FIG. 6 that by rotating the pinion gear 94 about its axis 92, the pusher member 82 can be either advanced in the distal direction or retracted therefrom. In the view of FIG. 6, the tubular pusher 82 is shown in its fully retracted position, its distal end 96 being slightly proximal of the proximal end edge of the mass of hemostatic material 82. By simply rotating the pinion 94 in a counterclockwise direction (when viewed as in FIG. 6), the pusher member 82 will be advanced in the distal direction and will force the hemostatic mass 80 out from the distal end 78 of the outer sheath or barrel 76.

Figure 7:
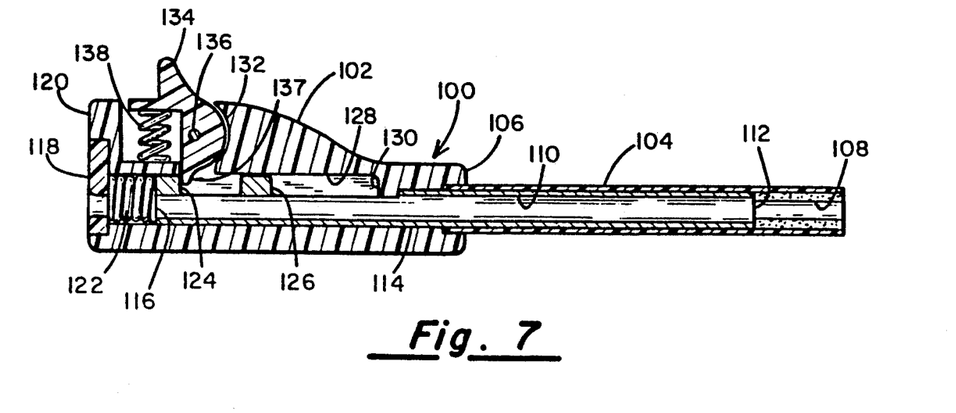
FIG. 7 is a side sectional view of the puncture sealing device in accordance with a fourth embodiment.

FIG. 7 discloses still another embodiment of the puncture sealing device of the present invention. That device is indicated generally by numeral 100 and it, too, is pictured without being mounted on a tubular member, such as a dilator, introducer, catheter, etc. It includes a molded plastic handle 102 supporting an outer tubular sheath or barrel 104 which projects longitudinally outward from the distal end 106 of the handle. As with the other embodiments, there is disposed near the distal end of the barrel 104, a mass of hemostatic material 108 which is preformed so as to be coaxially placeable about a tubular member.

Slidably received within the barrel 104 is a tubular pusher member 110, having its distal end 112 abutting or in closely spaced relationship to the proximal end of the hemostatic mass 108. The pusher member extends rearward into the handle 102 through a longitudinal bore 114 formed therein. Disposed between the proximal end 116 of the tubular pusher 110 and an insert 118 fitted into the proximal end 120 of the handle 102 is a compression spring 122. Projecting radially outward from the exterior surface of the pusher member 110 are first and second stop members 124 and 126. These stop members fit into a guideway 128 formed inwardly of the handle from the bore 114. At the distal end of the guideway 128 is a wall surface 130 which cooperates with the stop 126 to end the distal movement of the tubular pusher 110.

An arcuate recess 132 is formed in the handle and fitted into that recess is a molded plastic trigger 134 which is pivoted about a pin 136 to permit limited rotation thereof.

The puncture sealing device 100 is in its cocked position when the spring 122 is compressed between the insert 118 and the proximal end 116 of the pusher, as illustrated. It is held in this position by the engagement of a finger projection 137 on the trigger with the stop 124. A compression spring 138 cooperating between the handle 102 and the trigger 134 resists counterclockwise rotation of the trigger 134. However, when the surgeon pulls back on the upwardly protruding end of the trigger 134, it compresses the spring 138 and rotates the finger 137 out of contact with the stop 124, allowing the spring 122 to move the tubular pusher 110 in the distal direction to thereby eject the mass of hemostatic material 108 out the distal end of the tubular sheath 104.

While each of the embodiments of the invention disclosed thus far expose the hemostatic material by ejecting same out of the distal end of a tubular sheath or barrel by the action of a movable pusher member, the hemostatic material may also be exposed by holding the tubular pusher stationary and retracting the outer barrel or sheath in a proximal direction. In this regard, reference is made to FIG. 9 which shows a top elevation view of a PSD device of the latter type. The device is indicated generally by numeral 158 and it is seen to include an outer sheath 160 having its proximal end 162 attached to a hub 164. This hub is surrounded by a rotatable collar 166 having an integrally formed knob 168 thereon to facilitate its rotation. The collar 166 includes a helical thread groove 170 in its outer surface with the knob being journaled for rotation on the hub 164. The hemostatic mass is identified by numeral 172 in FIG. 9 and it is shown as being contained within the confines of the outer sheath 160 near its distal end 163. The distal end 163 is preferably slit so as to be expansible, thereby allowing the instrument to be used with tubular supports of differing French size. Also contained within the tubular sheath 160 is a tubular pusher 174 having a lumen 176 coaxially aligned with a central bore 178 formed longitudinally through the hemostatic mass 172. A wing-shaped fingergrip member 180 has a longitudinal bore 182 passing through it of a size to loosely surround the O.D. of the tubular sheath 160. The fingergrip member 180 is attached by means of a pin (not shown) which passes through the longitudinal slit 184 formed through the wall of the outer tubular sheath 160.

Figure 9:
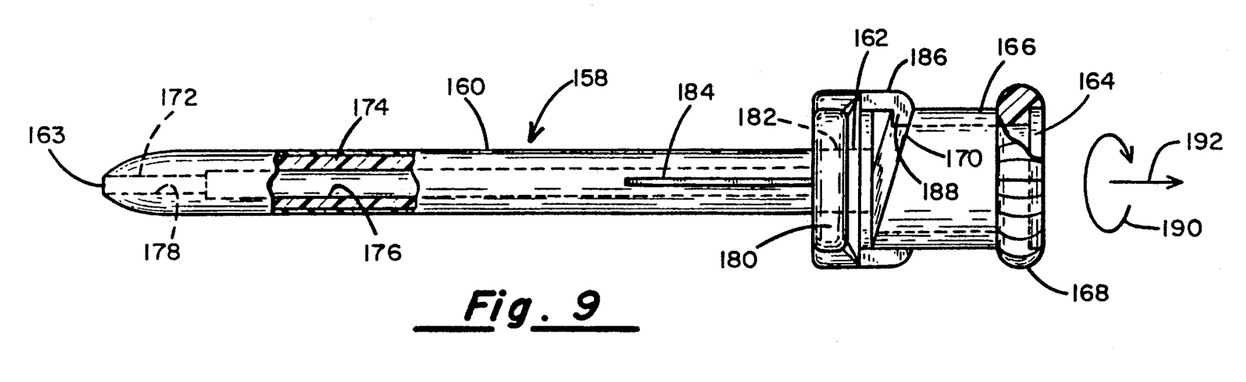
FIG. 9 is an enlarged view of an alternative design for a puncture sealing device in accordance with the invention.

Projecting longitudinally from the proximal side of the fingergrip member 180 is a narrow arm 186 which terminates in a radially extending finger 188. The finger 188 is arranged to ride in the helical groove or thread 170. It normally latches the fingergrips 180 and its attached pusher member 174 relative to the knob 168 which is operatively coupled to the outer sleeve 160.

To deploy the hemostatic mass, the surgeon will first grip the fingergrip member 180 with his index finger and forefinger of one hand while at the same time rotating the knob 166 in the direction represented by arrow 190. In doing so, the finger 188 will follow the helical groove 170 as the hub 164 moves in the direction of arrow 192. Once the finger 188 clears the helical groove 170, the surgeon may, by holding the fingergrip stationary and retracting the knob 168 in the proximal direction, withdraw the sheath 160 from its covering relation relative to the hemostatic mass 172. The sheath may also be formed with an averting distal end which can be made to roll back proximally to expose the hemostatic mass surrounding the coaxially disposed tubular member.

Moreover, it is envisioned that once the mass of hemostatic material has been appropriately positioned relative to the puncture to be sealed by advancing it within the confines of its tubular sheath, it may be exposed to blood and body fluids by providing a peelaway sheath not unlike the sheath arrangement disclosed in the U.S. Pat. No. 4,166,469 to Littleford.

Figure 10:
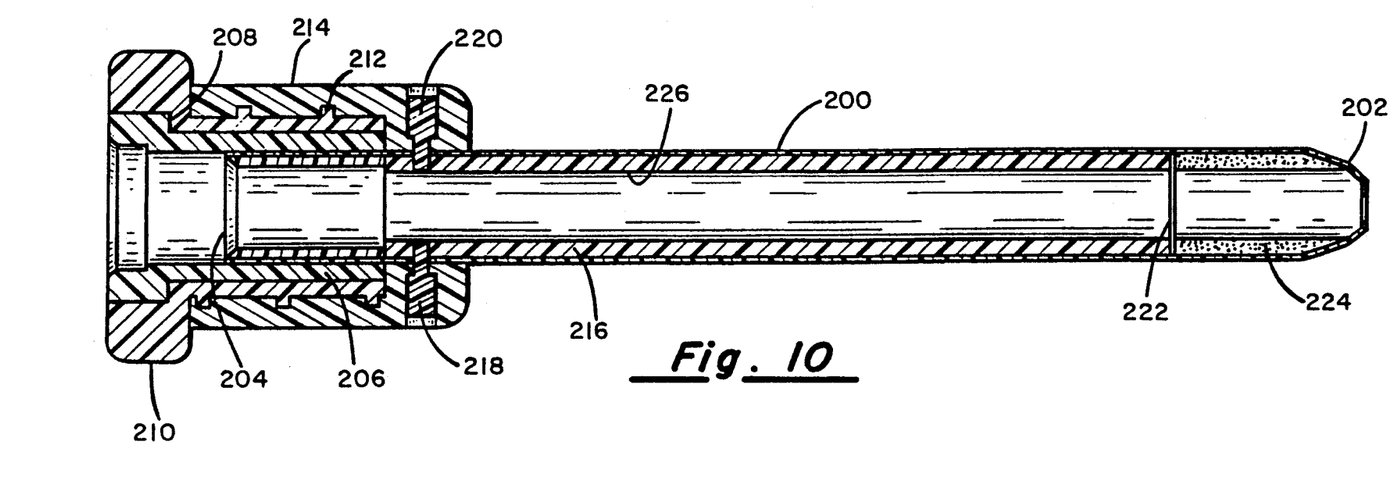
FIG. 10 is an enlarged view of yet another alternative design for a puncture sealing device in accordance with the invention.

FIG. 10 is an enlarged view of yet another implementation of the preferred embodiment of the present invention. It, too, includes an outer tubular sheath 200 formed from a suitable medical grade plastic and which has a somewhat bullet-shaped distal end 202 and a proximal end 04 which is suitably bonded to an inner tubular hub 206 so as to move with it. The inner hub 206 has a shoulder 208 cooperating with an annular recess formed in a rotatable knob 210. The knob 210 includes external threads 212 cooperating with mating thread grooves formed into the inner cylindrical wall of an outer hub member 214.

Disposed within the lumen of the outer sheath 200 is a tubular pusher 216 which is coupled to the outer hub member 214 by means of pins as at 218 and 220. Positioned beyond the distal end 222 of the tubular pusher 216 is a tubular mass of hemostatic material 224, preferably collagen. The diameter of the lumen 226 of the pusher member 216 and of the hemostatic mass 224 allows the assembly to fit over a further structure, such as a guidewire, an introducer, or a catheter body, all as previously described. The distal end of the outer sheath 200 is tapered to a reduced diameter and designed to cooperate with the O.D. of the device which the PSD is designed to cooperate. That is to say, the outer sheath 200 is adapted to engage the O.D. of the device with which it is used at its distal end to thereby create a seal preventing the premature ingress of body fluids that might react with the collagen plug 224.

To fire the device of FIG. 10, the user grips the outer hub 214 while rotating the knob 210 in the counterclockwise direction. As the knob 210 unscrews from the outer hub 214, it retracts the inner hub 206 with it due to the engagement of the shoulder 208 with the annular recess of the knob 210. Hence, the inner hub 206 and the sheath attached to it are also retracted in the proximal direction. The outer sheath may be slit so that the sheath may glide past the pins 218 and 220, but preferably, the sheath is designed so that it will readily split as it is drawn over the pins. By so designing the outer sheath, it eliminates the risk of blood leakage through preformed slits, such as shown in the embodiment of FIG. 9.

Once the sheath 200 is retracted to the point where its distal end 202 is at the proximal end 222 of the hemostatic mass 224, that mass is released within the puncture wound and the PSD can be removed, leaving the hemostatic mass in place. That mass quickly reacts with blood and other body fluids to swell closed so as to act as an effective block to the leakage of blood of the puncture wound.

OPERATION

Figure 8A:
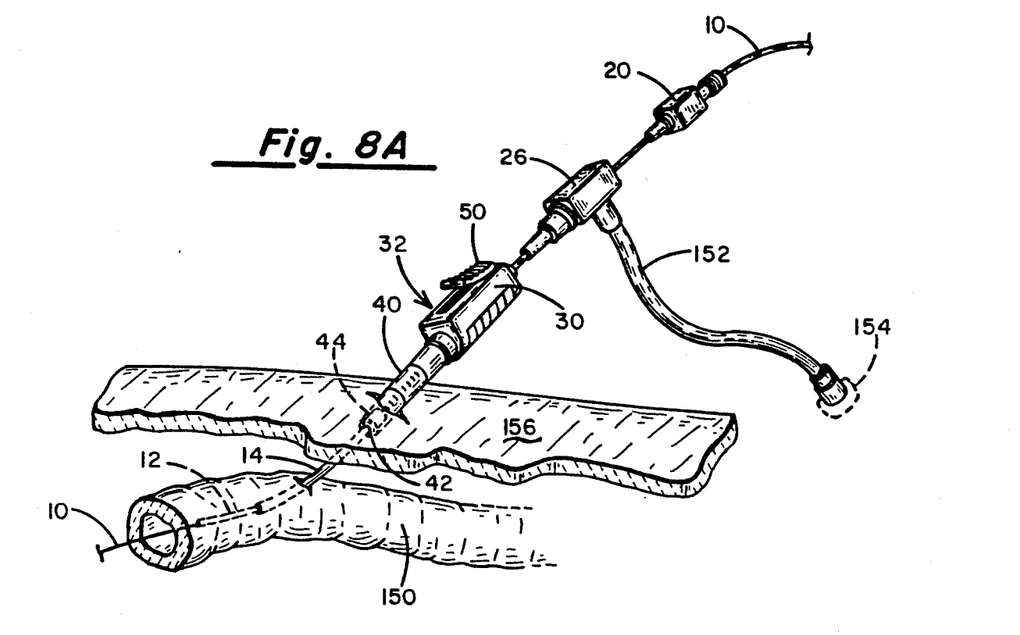
FIGS. 8A, 8B and 8C are perspective views of the device of the present invention helpful in understanding the method of use thereof.
Figure 8B:
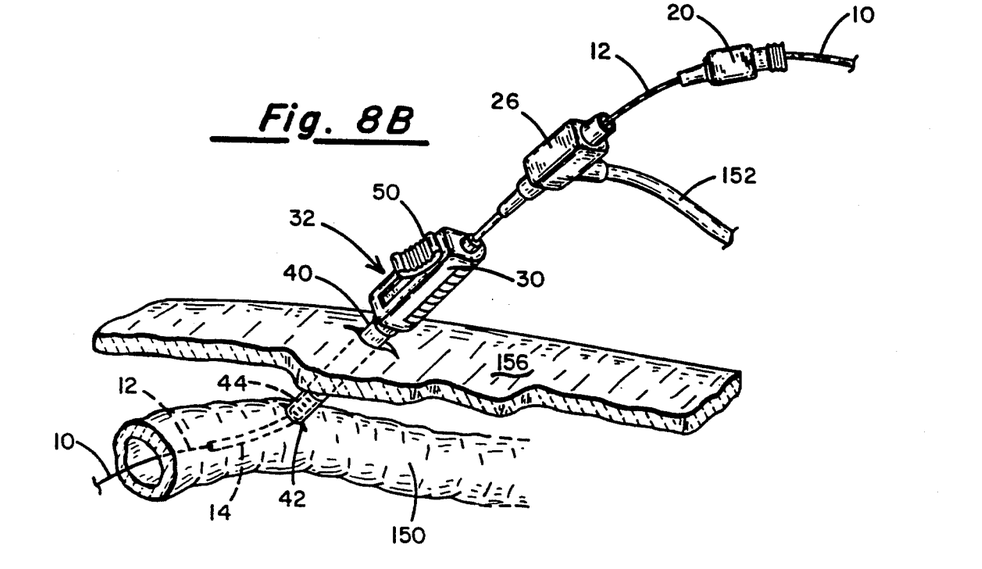
Figure 8C:
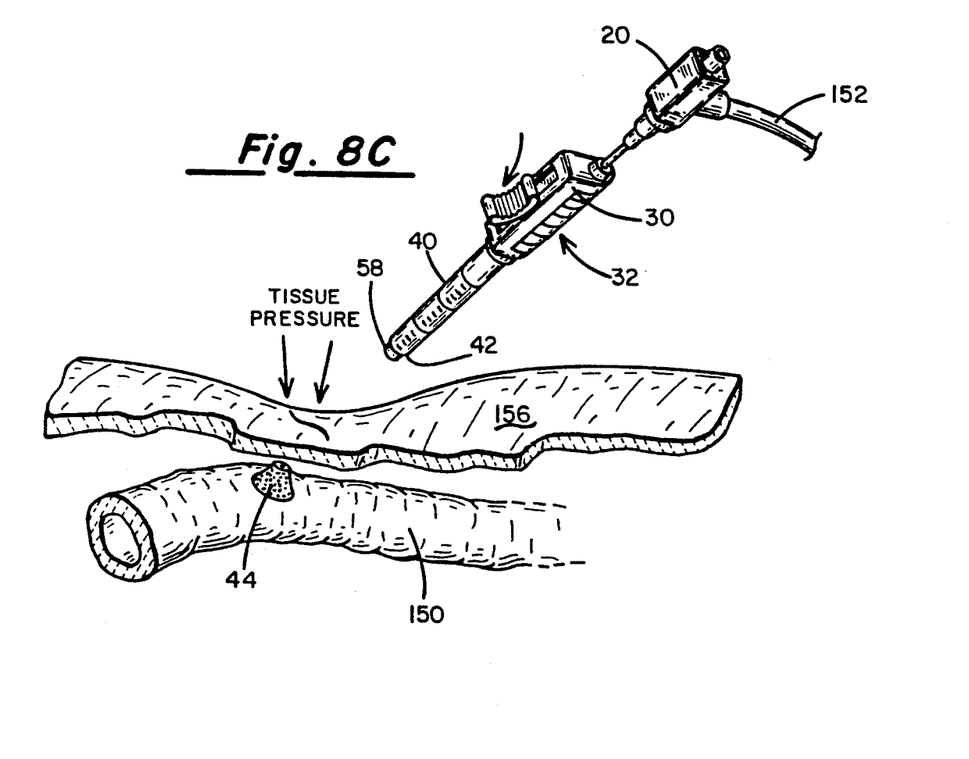

Referring next to FIGS. 8A through 8C, the mode of use of the PSD of FIG. 1 of the present invention will be explained. The operation and use of the other embodiments shown in FIGS. 6, 7, 9 and 10 will also be readily understood. Prior to the stage of the procedure represented by FIG. 8A, a standard percutaneous technique of inserting an angiographic needle into the selected blood vessel 150 has already been accomplished and the guidewire 10 is shown as having been inserted through the needle (not shown) and gently advanced to a desired depth within the vessel. Following that, the percutaneous needle is carefully slipped off the guidewire at its proximal end while the guidewire is being held in place. At this point, the dilator 12 will have been inserted completely into the lumen of the introducer 14.

Following that, and in accordance with the embodiment of FIG. 1, the dilator/introducer combination are inserted completely into the PSD indicated by numeral 32.

As is illustrated in FIGS. 8A through 8C, there is extending out from the hub 26 of the introducer 14 a flushing line 152, which is adapted to be coupled via a stopcock 154, to a suitable liquid supply. At this point, the assembly is inverted and flushed with heparinized or unheparinized saline solution so as to remove trapped air. Once the purge of air has been completed, the stopcock 154 is closed.

The open tip of the dilators and the accompanying introducer and PSD are now slipped onto the proximal end of the guidewire and fed over it to the point where the distal end of the dilator engages the blood vessel to be entered and a tactile response will be felt. The surgeon will by now have read the depth markings on either the percutaneous needle or the dilator and will make a mental note of same. FIG. 8A is at a stage where the tip of the tubular introducer 14 penetrates through the skin layer 156. By grasping the introducer near its distal tip end and close to the skin surface and while using a rotary motion, the dilator 12 and introducer 14 are made to pass along the guidewire and through the tissues so that they are each positioned within the lumen of the blood vessel as illustrated. The introducer sheath may now be further advanced to a desired position within the blood vessel.

Now, by grasping the PSD 32 near its distal tip end 42 close to the skin surface and using a rotary motion, the PSD is advanced along the introducer in the distal direction and through the tissue 156 until the distal end of the PSD is tactilely determined to be up against the outside of the vessel wall at the puncture sight. The scale markings on the sheath can be used to measure off the distance previously noted when the dilator was first inserted helping to confirm the desired placement of the distal end of the sheath. See FIG. 8B.

Holding the introducer sheath and the puncture seal device in place by installing a suture through the suture loop 37 on the handle 30 and through the patient's skin or other appropriate means, the surgeon now withdraws the guidewire and the dilator, whereby a working catheter can now be inserted through the lumen of the introducer and the catheterization procedure can be completed using standard techniques.

Following the conclusion of the chatheterization procedure, the surgeon will again confirm that the position of the tip of the PSD 32 and therefore the yet unreleased hemostatic material is up against the outside of the vessel wall at the puncture sight. Once that has been done, all of the devices, e.g., the working catheter and guidewire, are removed from the introducer 14 and the locking pin 62 or other "safety" device is released. The slide 52 is advanced in the distal direction by applying thumb pressure to the thumb pad 50 as the handle and attached tubular sheath of the PSD are pulled back a corresponding amount. The hemostatic mass becomes fully deployed by advancing the slide forward until the mass is ejected from the split distal end of the tubular sheath 40. While compressing the tissue around the puncture sight at the tip end of the PSD and holding it in position, the introducer 14 is now removed from the proximal end of the PSD. After a short delay, and while keeping the tissue compressed around the puncture site, the PSD sheath 40 is removed leaving the hemostatic seal 44 behind (FIG. 8C). Manual pressure is maintained on the puncture sight for approximately five minutes at which point it is relieved and an observation made as to whether the flow of blood has ceased.

The above procedure may be appropriately modified when the PSD shown in the embodiment of FIG. 4 is employed. In particular, the guidewire, dilator and introducer sheath may be made to enter the lumen of the blood vessel before the PSD 32 of FIG. 4 is coupled onto the exterior surface of the tubular introducer, given the fact that the longitudinal slots 64 and 66 in the device 32 and the coaxial hemostatic mass 44 allow the device to be slipped onto the introducer from the side rather than from the end. Those skilled in the art will also appreciate that the device of FIGS. 4 and 5 can be assembled onto the body of a working catheter already fitted into the working lumen of an endoscope and used to deposit a plug of hemostatic material against a bleeding blood vessel which may be observed during the course of the endoscopic procedure.

While the embodiments illustrated in FIGS. 1, 4, 6, 7 and 9 are sized and configured to seal a puncture wound in a blood vessel disposed a relatively short distance below the skin surface, those skilled in the art will appreciate that the dimensions of these devices may be changed, especially the lengths of the outer tubular sheath and pusher so that the puncture seal device may be used when carrying out any number of surgical procedures. For example, during the course of a laparoscopic cholecystectomy, should a blood vessel accidentally be nicked, the instrument of the present invention may be used to stem the flow of blood therefrom. In particular, by providing an elongated sheath or barrel having a mass of hemostatic material near its distal end and by providing a concentrically disposed probe, the instrument may be directed through a laparoscope or through one of the several trocars used in carrying out the procedure to approach the bleeder until the distal end of the PSD is juxtaposed with it. When appropriately positioned, the slide mechanism or other actuator for the tubular pusher can be activated to expose at least a portion of the coaxially located hemostatic material from the confines of the sheath while it is being pressed against the exterior wall of the bleeding vessel. After a few minutes, the slide mechanism in the handle can be further actuated to totally release the mass from the distal end of the device.

It is also envisioned that the distal tip of the tubular sheath can be configured in a variety of ways. Specifically disclosed herein are tubular sheaths having rounded, blunt and beveled ends. It is also contemplated that the distal end of the tubular sheath may have a V-shaped notch formed therein, which is particularly efficacious when it is desired to have the tip end straddle the blood vessel as the sealing procedure is performed. Still other shapes may permit a portion of the distal end of the outer tubular sheath to physically enter the puncture, serving to stabilize the distal end of the instrument.

As an alternative to providing a suture loop 37 on the handle for facilitating the device being locked in place by passing a suture through the skin and through this loop, it is also feasible to prevent the instrument of the present invention from being displaced during the course of a surgical procedure by providing a coarse, helical thread-like pattern on the exterior surface of the outer tubular sheath 40. When an instrument having this feature is effectively screwed into the skin and underlying tissue to the point where a tactile sensation indicates that its distal end abuts the blood vessel to be sealed, the increased friction afforded by the roughened surface inhibits the tendency for the instrument to slip out of the wound.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A surgical delivery instrument for delivering a hemostatic substance subcutaneously against a penetration site in a wall of a blood vessel in the course of a surgical procedure in which an incision is made through the blood vessel and a tubular body with an exterior wall is passed through said incision into said blood vessel, comprising:
   (a) an outer tubular sheath member having a proximal end, a distal end and a lumen extending therebetween, the diameter of said lumen being of a predetermined size greater than that of said tubular body and adapted to allow said tubular body to pass coaxially therethrough;
   (b) a housing affixed to said proximal end of said tubular outer sheath member, said housing including a tubular handle;
   (c) an annular mass of a hemostatic material, said mass having a proximal and a distal edge surface and initially being contained within said outer tubular sheath member proximate said distal end thereof so as to be isolated from exposure to body fluids and adapted to coaxially surround and slide longitudinally relative to the exterior wall of said tubular body upon insertion of said tubular sheath into said incision;
   (d) an inner tubular member reciprocally movable relative to said outer tubular sheath member and within said lumen of said outer tubular sheath member, said inner tubular member being concentrically disposed relative to said outer tubular sheath member and having a wall thickness for engaging said proximal edge surface of said mass as said inner tubular member is moved relative to said outer tubular sheath; and
   (e) a reciprocally movable slide mounted in said housing and operatively coupled to said inner tubular member for imparting relative movement in the longitudinal direction of said inner tubular member and said outer tubular sheath for exposing said mass to body fluids exterior of said lumen with said distal edge surface of said annular mass against the exterior wall of said blood vessel at said penetration site and with no portion of said hemostatic mass or said surgical delivery instrument entering into said blood vessel.

2. A surgical delivery instrument for delivering a hemostatic substance subcutaneously against a penetration site in a wall of a blood vessel in the course of a surgical procedure in which an incision is made through the blood vessel and a tubular body with an exterior wall is passed through said incision into said blood vessel, comprising:
   (a) an outer tubular sheath member having a proximal end, a distal end and a lumen extending therebetween, the diameter of said lumen being of a predetermined size greater than that of said tubular body and adapted to allow said tubular body to pass coaxially therethrough;
   (b) a housing affixed to said proximal end of said tubular outer sheath member, said housing including a tubular handle having a wall surface defining a longitudinal bore with an arcuate slot formed through said wall surface and communicating with said bore and with a manually rotatable gear journaled in said arcuate slot;
   (c) an annular mass of a hemostatic material, said mass having a proximal and a distal edge surface and initially being contained within said outer tubular sheath member proximate said distal end thereof so as to be isolated from exposure to body fluids and adapted to coaxially surround and slide longitudinally relative to the exterior wall of said tubular body upon insertion of said tubular sheath into said incision;
   (d) an inner tubular member reciprocally movable relative to said outer tubular sheath member and within said lumen of said outer tubular sheath member, said inner tubular member being concentrically disposed relative to said outer tubular sheath member and having a wall thickness for engaging said proximal edge surface of said mass as said inner tubular member is moved relative to said outer tubular sheath; and
   (e) reciprocally movable slide mounted in said housing and including a gear rack affixed to said inner tubular member operatively coupled to said gear for imparting relative movement in the longitudinal direction of said inner tubular member and said outer tubular sheath for exposing said mass to body fluids exterior of said lumen with said distal edge surface of said annular mass against the exterior wall of said blood vessel at said penetration site and with no portion of said hemostatic mass or said surgical delivery instrument entering into said blood vessel.

3. A surgical delivery instrument for delivering a hemostatic substance subcutaneously against a penetration site in a wall of a blood vessel in the course of a surgical procedure in which an incision is made through the blood vessel and a tubular body with an exterior wall is passed through said incision into said blood vessel, comprising:
   (a) an outer tubular sheath member having a proximal end, a distal end and a lumen extending therebetween, the diameter of said lumen being of a predetermined size greater than that of said tubular body and adapted to allow said tubular body to pass coaxially therethrough;
   (b) a housing affixed to said proximal end of said outer tubular sheath member, said housing including a tubular handle, said tubular handle having a wall surface defining a longitudinal bore and an arcuate slot formed through said wall surface to communicate with said bore;
   (c) an annular mass of a hemostatic material, said mass having a proximal and a distal edge surface and initially being contained within said outer tubular sheath member proximate said distal end thereof so as to be isolated from exposure to body fluids and adapted to coaxially surround and slide longitudinally relative to the exterior wall of said tubular body upon insertion of said tubular sheath into said incision;

(d) an inner tubular member reciprocally movable relative to said outer tubular sheath member and within said lumen of said outer tubular sheath member, said inner tubular member being partially contained in said longitudinal bore of said tubular handle, said inner tubular member being concentrically disposed relative to said outer tubular sheath member and having a wall thickness for engaging said proximal edge surface of said mass as said inner tubular member is moved relative to said outer tubular sheath;

(e) a reciprocally movable slide mounted in said housing and including a stop member affixed to said inner tubular member with a spring means disposed within said handle and cooperating with said inner tubular member for applying a distally directed force to said inner tubular member for imparting relative movement in the longitudinal direction of said inner tubular member and said outer tubular sheath for exposing said mass fluids exterior of said lumen with said distal edge surface of said annular mass against the exterior wall of said blood vessel at said penetration site and with no portion of said hemostatic mass or said surgical delivery instrument entering into said blood vessel; and (f) trigger means disposed on said handle for selectively releasing said force.

4. A surgical delivery instrument for delivering a hemostatic substance subcutaneously against a penetration site in a wall of a blood vessel in the course of a surgical procedure in which an incision is made through the blood vessel and a tubular body with an exterior wall is passed through said incision into said blood vessel, comprising:

(a) an outer tubular sheath member having a proximal end, a distal end and a lumen extending therebetween, the diameter of said lumen being of a predetermined size greater than that of said tubular body and adapted to allow said tubular body to pass coaxially therethrough;

(b) a housing including a tubular handle affixed to said proximal end of said tubular outer sheath member;

(c) an annular mass of a hemostatic material, said mass having a proximal and a distal edge surface and initially being contained within said outer tubular sheath member proximate said distal end thereof so as to be isolated from exposure to body fluids and adapted to coaxially surround and slide longitudinally relative to the exterior wall of said tubular body upon insertion of said tubular sheath into said incision;

(d) an inner tubular member reciprocally movable relative to said outer tubular sheath member and within said lumen of said outer tubular sheath member, said inner tubular member being concentrically disposed relative to said outer tubular sheath member and having a wall thickness for engaging said proximal edge surface of said mass as said inner tubular member is moved relative to said outer tubular sheath; and (e) a reciprocally movable slide mounted in said housing, said outer tubular sheath member, said mass, said inner tubular member, said housing and said slide each including a longitudinal slot aligned with one another for receiving said tubular body therein, said slide being operatively coupled to said inner tubular member for imparting relative movement in the longitudinal direction of said inner tubular member and said outer tubular sheath for exposing said mass to body fluids exterior of said lumen with said distal edge surface of said annular mass against the exterior wall of said blood vessel at said penetration site and with no portion of said hemostatic mass or said surgical delivery instrument entering into said blood vessel.

5. A surgical delivery instrument for delivering a hemostatic substance subcutaneously against a wound opening in a wall of a blood vessel during the course of a catheterization, laparoscopic or endoscopic procedure in which an incision is made through the skin and into said blood vessel wall, comprising:

(a) a first tubular member having a distal end adapted to be received into said incision;

(b) an outer tubular sheath member having a proximal end, a beveled distal end and a wall surface defining a lumen extending between said proximal and distal ends, said lumen being of a size which allows said first tubular member to be coaxially received therein;

(c) a housing affixed to said proximal end of said outer tubular sheath member;

(d) an annular shaped mass formed from a hemostatic material and having a proximal edge surface and a distal edge surface conforming to said beveled distal end of said tubular sheath member, said mass being sized to prevent entry through said incision into said blood vessel and initially disposed within said sheath in coaxial surrounding relation relative to said first tubular member and isolated from exposure to body fluids by said sheath;

(e) a tubular pusher reciprocally movable relative to and within said lumen of said outer tubular sheath member, said pusher being concentrically disposed relative to said outer tubular sheath member and having a wall thickness for engaging said proximal edge surface of said mass;

(f) a reciprocally slidable member operatively coupled between said housing and said tubular pusher for imparting longitudinal movement to said tubular pusher for ejecting said mass outward from said lumen at said distal end of said outer tubular sheath member along said first tubular member with said beveled distal edge surface against the exterior wall of said blood vessel at the site of said incision and with no portion of said mass entering said blood vessel.

6. A surgical delivery instrument for delivering a hemostatic substance subcutaneously against a wound opening in a wall of a blood vessel during the course of a catheterization, laparoscopic or endoscopic procedure in which an incision is made through the skin and into said blood vessel wall, comprising:

(a) a first tubular member having a distal end adapted to be received into said incision;

(b) an outer tubular sheath member having a proximal end, a distal end and a wall surface defining a lumen extending between said proximal and distal ends, said lumen being of a size which allows said first tubular member to be coaxially received therein;

(c) said outer tubular sheath member having a cylindrical hub affixed to said proximal end thereof and there being a longitudinal slot formed through said wall surface of said outer tubular sheath member proximate said proximal end thereof;

(d) a knob journaled for rotation about said cylindrical hub, said knob including a helical groove on a portion of an exterior surface thereof;

(e) an annular shaped mass formed from a hemostatic material and having a proximal edge surface and a distal edge surface, said mass being initially disposed within said sheath in coaxial surrounding relation relative to said first tubular member and isolated from exposure to body fluids by said sheath; and (f) a tubular pusher reciprocally movable relative to and within said lumen of said outer tubular sheath member, said tubular pusher having a finger grip member coupled to it through said longitudinal slot, said finger grip further including a follower member engaging said helical groove, said tubular pusher being concentrically disposed relative to said outer tubular sheath member and having a wall thickness for engaging said proximal edge surface of said mass, imparting longitudinal movement to said tubular pusher for ejecting said mass outward from said lumen at said distal end of said sheath along said first tubular member and against an exterior portion of said wall of said blood vessel at the site of said incision when said knob is first rotated so that said follower member clears said helical groove and is then pulled longitudinally in a proximal direction while said finger grip member is held stationary.

7. A surgical instrument for delivering a hemostatic substance subcutaneously against a wound opening in a wall of a blood vessel during the course of a catheterization or endoscopic procedure in which an incision is made through the skin and into said blood vessel wall, comprising:

(a) a tubular outer sheath member having a proximal end, an open distal end and a lumen extending therebetween;

(b) an inner tubular hub affixed to said proximal end of said tubular outer sheath member;

(c) a tubular pusher coaxially disposed within said lumen of said outer tubular sheath member and of a length less than that of said tubular outer sheath member;

(d) an annular mass of hemostatic material disposed between a distal end of said pusher and said distal end of said tubular sheath;

(e) an outer tubular hub secured to said tubular pusher by a coupling passing radially through said outer sheath; and (f) a knob rotatably supported on said inner hub and having screw threads engaging said outer hub for imparting translational movement to said inner hub relative to said outer hub upon rotation of said knob.

8. The surgical instrument as in claim 7 wherein said rotatable knob includes an externally threaded tubular shank, the threads engaging a helical groove formed in said tubular outer hub.

9. The surgical instrument as in claim 8 wherein said tubular inner hub includes an annular flange cooperating with an annular shoulder formed on said rotatable knob.

10. The surgical instrument as in claim 7 wherein said outer tubular hub is coupled to said tubular pusher by at least one pin extending radially through said tubular outer sheath.

11. A method for effecting hemostasis of a bleeding blood vessel during the course of a surgical procedure comprising the steps of:

(a) providing a puncture seal device having an elongated tubular outer sheath with a distal end and a longitudinal slot extending the length thereof, said tubular outer sheath surrounding a tubular pusher member and a mass of hemostatic material disposed distally and coaxially of said tubular pusher member within said tubular outer sheath, said tubular pusher member and said mass each also having a slot formed longitudinally therein, the slots in said pusher member and in said mass being in longitudinal alignment with said longitudinal slot in said tubular outer sheath;

(b) providing a tubular body having a distal end and a working lumen extending the length thereof;

(c) positioning the distal end of said tubular body adjacent said bleeding blood vessel;

(d) coupling said puncture seal device to said tubular body by inserting said tubular body into said aligned slots;

(e) advancing said puncture seal device in the distal direction along said tubular body until the distal end of said tubular outer sheath is closely proximate said bleeding vessel; and (f) advancing said tubular pusher member relative to said tubular outer sheath to force said mass out of said tubular outer sheath and into contact with the bleeding blood vessel.

* * * * *

UNITED STATES PATENT AND TRADEMARK OFFICE
CERTIFICATE OF CORRECTION

PATENT NO. : 5,324,306
DATED : June 28, 1994
INVENTOR(S) : Joshua Makower et al

It is certified that error appears in the above-indentified patent and that said Letters Patent is hereby corrected as shown below:

```
Column 13,   (b) line 31 replace "tubular outer" with
   -- outer tubular --;
Column 14,   (b) line 8  replace "tubular outer" with
   -- outer tubular --;
Column 14,   (e) line 32 insert -- a -- before "reciprocally";
Column 15,   (b) line 45 replace "tubular outer" with
   --outer tubular --;
Column 18,   line 12 replace "tubular outer" with
   -- outer tubular --;
Column 18,   line 14 replace "tubular inner" with
   -- inner tubular --.
```

Signed and Sealed this

Thirteenth Day of September, 1994

Attest:

BRUCE LEHMAN

Attesting Officer           Commissioner of Patents and Trademarks